(12) United States Patent
Fremerey

(10) Patent No.: US 6,581,476 B1
(45) Date of Patent: *Jun. 24, 2003

(54) MEASURING APPARATUS

(75) Inventor: Johan K. Fremerey, Bonn (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/552,783

(22) Filed: Apr. 20, 2000

(30) Foreign Application Priority Data

Sep. 18, 1999 (DE) .......................... 199 44 863

(51) Int. Cl.⁷ .............................. G01F 15/00
(52) U.S. Cl. .................................. 73/861.77
(58) Field of Search .................. 73/861.77, 861.78, 73/861.79, 861.83, 861.75, 861.08, 861.13; 417/365, 352, 423.12; 310/90.5

(56) References Cited

U.S. PATENT DOCUMENTS

| | | | |
|---|---|---|---|
| 3,512,851 A | | 5/1970 | Love et al. |
| 3,614,181 A | * | 10/1971 | Meeks .......................... 308/10 |
| 3,623,835 A | | 11/1971 | Boyd |
| 4,057,369 A | * | 11/1977 | Isenberg et al. ............ 417/365 |
| 4,398,773 A | | 8/1983 | Boden et al. |
| 4,688,998 A | * | 8/1987 | Olsen et al. ................ 417/365 |
| 4,763,032 A | * | 8/1988 | Bramm et al. ............... 310/905 |
| 4,779,614 A | * | 10/1988 | Moise .......................... 600/16 |
| 4,812,694 A | | 3/1989 | Fremery |
| 4,948,348 A | * | 8/1990 | Doll et al. .................. 417/365 |
| 5,126,610 A | | 6/1992 | Fremerey |
| 5,211,546 A | | 5/1993 | Isaacson et al. |
| 5,385,581 A | | 1/1995 | Bramm et al. |
| 5,695,471 A | | 12/1997 | Wampler |

FOREIGN PATENT DOCUMENTS

| | | |
|---|---|---|
| DE | 24 44 099 A1 | 1/1976 |
| DE | 25 37 367 C3 | 4/1976 |
| DE | 24 57 783 C2 | 6/1976 |
| DE | 29 19 236 A1 | 11/1980 |
| EP | 0 856 666 A1 | 8/1998 |
| EP | 0 882 427 A1 | 12/1998 |
| GB | 2 057 590 | 4/1981 |
| GB | 2 088 017 A | 6/1982 |
| WO | WO 92/15795 | 9/1992 |

OTHER PUBLICATIONS

"A Fluid Dynamic Analysis Using Flow . . . " by Wernicke et al. (Artificial Organs (19(2) 161–177, 1995).

* cited by examiner

Primary Examiner—Hezron Williams
Assistant Examiner—C Dickens
(74) Attorney, Agent, or Firm—Herbert Dubno

(57) ABSTRACT

The invention relates to a measuring apparatus (1) for fluids with the following features:

a) the measuring apparatus (1) has a support tube (2);

b) a rotor (3, 36, 42) is rotatably journaled in the support tube (2);

c) the rotor (3, 36, 42) is configured for interaction with the fluid found in the support tube (2);

d) the rotor (3, 36, 42) has at both ends axially-magnetized permanently magnetic rotor magnets (7, 8; 46; 47);

e) permanent magnetic stator magnets (18, 19; 52, 53) connected with the support tube (2) are axially juxtaposed with the ends of the rotor (3, 36, 42);

f) each stator magnet (18, 19; 52, 53) has such axial magnetization that the neighboring stator and rotor magnets (18, 19; 7, 8; 46, 47; 52, 53) are oppositely attractive.

g) the rotor device (1 [sic]) has a magnetic axially-stabilizing device (22, 23, 27; 58, 59, 66) for the rotor (3, 36, 42).

18 Claims, 3 Drawing Sheets

US 6,581,476 B1

MEASURING APPARATUS

FIELD OF THE INVENTION

The invention relates to a measuring apparatus for fluids, it being understood that under "fluids", both a gas and also a liquid are encompassed.

BACKGROUND OF THE INVENTION

In the state of the art, measuring apparatuses have been developed in which a rotor is maintained in an equilibrium position within a carrier tube by magnetic field forces. Thus in DE-A-29 19 236, a turbine wheel counter is described for the flow-through measurement of liquids in which the rotor has, for radial stability, two spaced apart rotor magnets formed as permanent magnets which are juxtaposed pairwise with stator magnets also formed as permanent magnets, which surround the carrier tube. Thus the rotor magnets and stator magnets are magnetized in the axial direction so as to repel one another.

Between the stator magnets, an electromagnet coil is arranged which surrounds the carrier tube in an annular manner. The magnet coil cooperates with a ferromagnetic flux conductive piece on the rotor which is arranged between the rotor magnets.

Additionally, a sensor is provided that detects the axial position of the rotor and cooperates with a control unit which regulates the electric current flow in the magnet coil. As soon as the field forces of the rotor magnets and the stator magnets are engendered by an axial shift of the rotor to accelerate the rotor out of the equilibrium position in the axial direction there is generated a signal of the axial shift of the rotor as measured by the sensor which produces in the magnet coil a counteracting stabilizing field force. The rotor is thus, upon an axial shift in position in one or the other direction, always returned to its setpoint position. The stabilizing axial force countering the axial shift is so phase-shifted in time in a known manner that the rotor is held stably in its setpoint position by restoring as well as damping forces.

A drawback of the aforedescribed measuring device is that the rotor has only a relatively limited positional stiffness in the radial direction. The origin of that problem is the large distance between the stator and rotor magnets because of the annular channel between the support pipe and the rotor for the throughflow of the fluid.

In DE-A-24 44 099, a magnetic bearing for rapidly movable bodies is described. This magnetic bearing has a sleeve-shaped rotor whose ends have pole pieces provided with permanent magnets and whereby, based upon tractive forces on the rotor, the latter is held in a stable position. By means of a contactless position sensor, deviations from the equilibrium position are determined. Such deviations are compared by a powerless electromagnetic stray field control for which annular coils are provided which are arranged proximal to the gaps on the pole pieces of the rotor. Such a magnetic bearing is not suitable for disposition in a carrier tube through which a fluid is conducted on spatial grounds.

Magnetic bearings have also been used for blood pumps. Thus in U.S. Pat. No. 5,695,471, a blood pump is known which is formed as a radial pump with a radial rotor. The radial rotor is disposed within a carrier tube and has in an inlet side extension, a multiplicity of rotor magnets which are juxtaposed with stator magnets on the carrier tube. Additionally the radial rotor has distributed over the periphery a multiplicity of rod-shaped rotor magnets extending in the axial direction and which are juxtaposed with ring-shaped stator magnets on both sides of the radial rotor toward the carrier tube. These rotor and stator magnets should support the radial journaling in the region of the extension of the rotor. In the axial direction, the rotor is held purely mechanically with one end on a ball and another end on a point journal. The rotor is driven by a brushless rotary field motor. On sides of the carrier tube a coil is arranged which cooperates with a spoked-wheel magnet set into the radial rotor. A drawback of this blood pump is that the bearing stability in the radial direction is not optimal and that the pump because of the multiplicity of rotor and stator magnets has a high spatial requirement and high weight. In addition, the purely mechanical bearings give rise to wear in the axial direction.

The are also axial blood pumps. Here the journaling is effected exclusively mechanically in impeller wheels which are arranged at fixed locations in the carrier pipe ahead of and behind the rotor (Wernicke et al., A Fluid Dynamic Analysis Using Flow Visualization of the Baylor/NASA Implantable Axial Flow Blood Pump for Design Improvement, Artificial Organs 19(2), 1995, Pages 161–177). Such mechanical bearings are subject to wear and have an unsatisfactory effect on sensitive liquids, especially body liquids like blood.

OBJECT OF THE INVENTION

An object of the invention is to provide a measuring device of the type described at the outset which has a substantially higher bearing stiffness, especially in the radial direction, and which therefore has numerous applications.

SUMMARY OF THE INVENTION

This object is achieved by the following features in accordance with the invention:

a) the measuring device has a carrier tube;
b) a rotor is journaled rotatably in the carrier tube;
c) the rotor is configured for interaction with the fluid found in the carrier tube;
d) the rotor has at both ends axially magnetized permanent magnet rotor magnets;
e) the ends of the rotor are juxtaposed with axially opposite permanently magnetic stator magnets connected to the carrier tube;
f) each stator magnet has such axial magnetism that it attracts the neighboring stator and rotor magnets; and
g) the measuring device has a magnetic axial stabilizing device for the rotor.

Alternatively, the object is achieved by a measuring device with the following features:

a) the measuring device has a carrier tube;
b) a rotor is rotatably journaled in the carrier tube;
c) the rotor is configured for the interaction with the fluid found in the carrier tube;
d) at the ends of the rotor there are respective axially magnetized permanently magnetic magnets opposite a flux conductive member whereby the magnets are either mounted on the rotor as rotor magnets or are connected to the carrier tube as stator magnets; and
e) the measuring device has a magnetic axial stabilizer unit.

The basic concept of the invention is thus, by means of rotor magnets and stator magnets arranged at the ends of the rotor, to generate a magnetic field in the axial direction respectively bridging the gaps between the rotor and stator magnets which respectively draws the opposing pairs of rotor and stator magnets in opposite directions toward one another. As a result, a bearing stiffness with the same geometry with respect to the magnet bearing of DE-A-29 19 236 can be obtained, but increased by at least one power of ten without thereby significantly affecting the annular passage between the carrier tube and the rotor hub. The aforedescribed effect also can be obtained when each magnet assembly has a magnet on one side and a flux-conducting device on the other side, as opposed to a system where each magnet assembly consists of two magnets, such as the rotor and stator magnets, which are juxtaposed. Thus, as an alternative, the magnet can be a rotor magnet mounted on the rotor and the flux-conducting member can be connected to the carrier tube or the flux-conducting member can be arranged on the rotor and the magnet fixed as a stator magnet on the carrier tube. For generating a high bearing stiffness, additional electric magnet coils can be provided for amplifying the magnetization of the flux-conducting member in the sense of increasing the attractive force between the magnets and the flux-conducting members.

To the extent that rotor and stator magnets pairwise are disposed opposite one another, they should preferably be composed of at least two interfitted partial magnets whereby respectively radially neighboring partial magnets are oppositely magnetized. Through this configuration of the rotor and stator magnets, a further increase in the bearing stiffness by a factor of 40 can be produced.

The rotor is preferably formed as an axial rotor so that there is an axial flow in the support tube. Such an axial rotor is substantially less expensive to shape than a radial rotor.

According to the invention, further, the rotor is provided with a rotor hub and the rotor magnets or flux guiding pieces are arranged in the rotor hub, whereby stator magnets or the flux-conducting pieces are disposed opposite the end faces of the rotor hub. The stator magnets or flux-conducting pieces can be connected with the carrier tube via ribs configured to promote flow. With this arrangement, a compact construction results which avoids to the greatest possible extent detrimental cracks. The stator magnets or flux-conductive pieces should be disposed in radial stabilizers whose contours do not project beyond the rotor hub whereby the radial stabilizers preferably have the same contours as the rotor hub.

In a further feature of the invention, at least one of the respective oppositely lying end faces of the radial stabilizers and the rotor can be of spherical configuration. With this configuration, it is possible to avoid, upon axial shifting of the rotor, a mechanical contact of axially spaced portions of the rotor and radial stabilizer. To limit the radial and/or axial mobility of the rotor it is advantageous to provide the respective oppositely lying end faces of the radial stabilizer and the rotor with mutually interdigitating complementary bearing pins and pin recesses, whereby a corresponding radial play is ensured such that bearing pins and bearing recesses will come into contact only upon relatively large deflections of the rotor in the radial direction.

According to a further feature of the invention, the rotor magnets and the stator magnets or flux-conducting pieces are arranged directly opposite one another respectively to ensure the strongest possible magnetic field.

According to the invention it is further proposed that the axial stabilization device have at least one electromagnetic coil as well as a control unit with a sensor detecting the axial movement of the rotor, whereby the control unit so influences the electric current flux in the magnet coil or the magnet coils that the magnetic field of the magnet coils counteracts an axial movement of the rotor out of its setpoint position. Such an axial stabilization device in principle is already known from DE-A-29 19 236 and DE-A-24 44 099 and has been found to be effective. Advantageously, the axial stabilizer can have two magnet coils which are arranged in the region of the stator magnets and/or the end faces of the rotor, whereby the axial stabilization is especially effective.

Thus there are two possibilities for arrangement of the magnet coils, namely, one in such manner that they surround the carrier tube and the second in which they are provided in the radial stabilizer itself whereby, however, then facilities must be provided for leading the conductors to and from the magnet coils. Preferably the magnetizable flux-conducting pieces of the radial stabilizer should be in such a configuration and arrangement that the axial magnetic field generated by the reactor and stator magnets is superimposed in the gap between the end of the radial stabilizer and reactor with the magnetic field generated by the magnet coils in axial direction and thus in a manner counteracting an axial movement of the rotor out of its intended position. The magnet coils can be used as sensors themselves. The flux-conducting pieces are preferably arranged at the level of the magnetic coils.

Advantageously the rotor has a pulse generator and the carrier tube a pulse pickup, whereby the pulse generator produces pulses detected by the pulse pickup and representing the speed of the rotor. This can be achieved in a simple manner by forming the pulse generator as pulse magnets and the pulse pickup as a coil so that in the coil an electric current is induced upon rotation of the rotor.

In a further feature of the invention it is provided that the carrier tube has at the level of the rotor, a three-phase stator which can be fed with three-phase current and the rotor has a radially magnetized plurality of spoked wheel magnet poles. The result is a synchronous motor which by supply of the three-phase stator with three-phase current generates a rotary field which entrains the rotor so that a rotary movement is imposed on the rotor. The measuring device in this case has motor properties. Preferably the magnets on the pole spokes are four magnetic segments magnetized in four different radial directions to counteract wobbling of the rotating rotor resulting from magnetic field asymmetry in the region of the bearing gap between rotor and radial stabilizer. The rotary field stator should be connected with an electronic three-phase generator operating with load angle regulation. The desired regulation of the load angle can be effective to set and stabilize the rotary field and torque applied to the motor depending upon the amount and direction of adjustment of the load angle.

The rotor can be matched to the respective purpose. For example, the rotor can have vane-type projections when the measuring device according to the invention is to be used as a centrifugal or turbine measuring unit for flowthrough measurements. The surface of the rotor can, however, be configured to be smooth and especially cylindrical, to the extent that the measuring device is configured in the aforedescribed manner as a synchronous motor for measurement of the viscosity of gaseous or liquid media by determining the electrical power utilized by the synchronous motor for maintaining a certain rotor speed. The viscosity is substantially proportional to the friction work at the outer surface of the motor so that the friction work in turn represents a measurement of the viscosity of the medium surrounding the rotor.

According to a further feature of the invention, it is proposed that the outer surface of the rotor have at least one radial outwardly extending projection and that a sensor is provided which detects the axial position of the rotor and generates a signal proportional to the axial position. The projection, preferably in the form of an annular rib, enables the possibility of measurement of the axial flow velocity of gaseous or liquid medium in which the axial force transmitted via the projection to the rotor is detected through the corresponding axial position shift of the rotor, whereby the axial stabilizing device generates a corresponding signal. Both features can be combined to the extent that the measuring device is provided with a synchronous motor in the above-described manner. Then the axial shift of the rotor and the drive power supplied to the rotor can be detected through the use of the synchronous motor so that both the flow velocity and the viscosity of the flow can be measured at the same time.

BRIEF DESCRIPTION OF THE DRAWING

Embodiments of the invention are detailed in the drawing. In the drawing.

SPECIFIC DESCRIPTION

Figure 1:
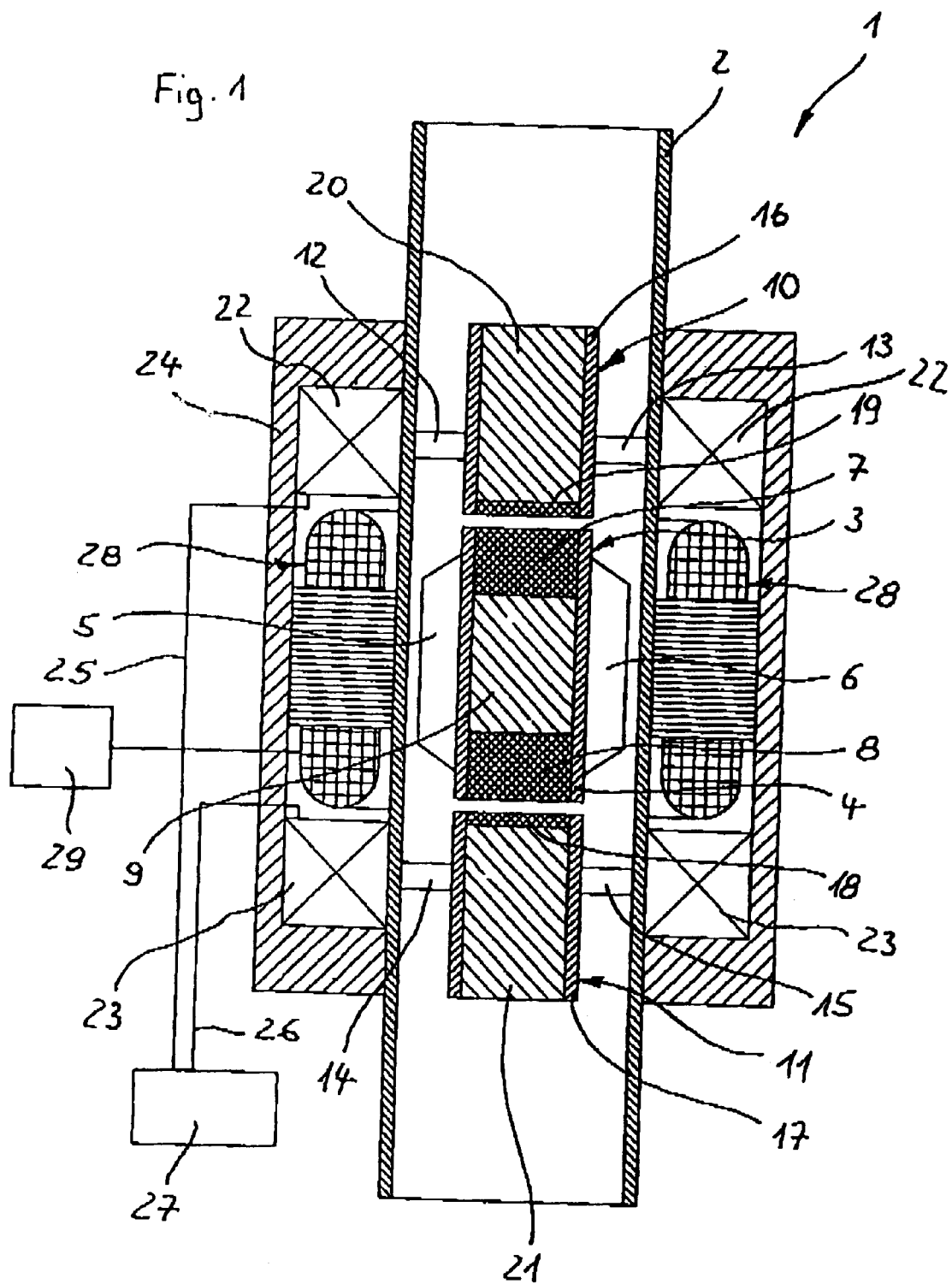
FIG. 1 is a longitudinal section through the measuring device of the invention.

FIG. 1 shows a measuring apparatus which has been designated at 1 overall and which can be built into a liquid or gas-carrying pipe. The measuring apparatus 1 has a cylindrical support type 2 which can be connected by flanges not shown in greater detail as an intermediate piece in the pipe so that the liquid or gas flows through the carrier tube 2.

A rotor 3 is disposed centrally in the carrier tube 2 and has a cylindrical rotor hub 4 on the exterior of which vanes 5, 6 are formed. In the end regions, the rotor hub 4 is provided with two rotor magnets 7 and 8 configured as permanent magnets which are axially magnetized. Between both rotor magnets 7, 8, a spoked wheel magnet 9 is located which is divided along its periphery into four radially magnetized segments.

Neighboring the two end faces of the rotor hub 4 are radial stabilizers 10, 11 which, via ribs 12, 13, 14, 15 are fastened on the interior of the carrier tube 2 coaxial with the rotor 3 so that it is axially symmetrical to the rotor 3. The radial stabilizers 10, 11 have cylindrical stabilizer sleeves 16, 17 whose diameters correspond to the diameter of the rotor hub 4. The radial stabilizers 10, 11 thus form, with respect to their outer contours, extensions of the rotor hub 4. The stabilizer sleeves 16, 17 enclose respective stator magnets 18, 19, formed as permanent magnets, in the region neighboring the rotor 3, whereby the stator magnets 18, 19 are so axially magnetized that in the gaps between the radial stabilizers 10, 11 and the rotor 3, an axially directed magnetic field results which attracts the rotor 3. These magnetic fields serve to ensure that the rotor 3 will always be held centrally to the axis of the support tube 2 so that possible radial deflections will be immediately reset. As a consequence, a high bearing stiffness results, in the radial direction.

The radial stabilizers 10 have additional ferromagnetic flux guide pieces 20, 21 which cooperate with annular electromagnet coils 22, 23 of an axial stabilizing device. The magnet coils 22, 23 are arranged at the levels of the flux guide pieces 20, 21 and surround the support tube 2 externally. They are seated in a housing 24 annularly surrounding the support tube 2 and which in the end regions serves simultaneously as flow guide pieces for the magnet flux of coils 22 and 23. The two magnet coils 22, 23 are connected via electric conductors 25, 26 with a control unit 27. The control unit 27 feeds the magnet coils 22, 23 with excitation current. As a result, the magnetic fluxes in the gaps between rotor 3 and the radial stabilizers 10, 11 are so superimposed and controlled that the rotor 3 assumes a contactless axially stable position on all sides between the radial stabilizers 10, 11. The magnet coils 22, 23 thus not only serve for flux circulation but simultaneously also as sensor coils for the contactless detection of the axial position of the rotor 3 in a manner identical to that in the magnetic bearing according to DE-A-24 44 099.

Between the two magnet coils 22, 23, an annular rotary field stator 28 is arranged in the housing 24 and together with the spoked pole magnet 9 forms a synchronous motor in the rotor 3. The rotary field stator 28 is, for this purpose, connected with an electronic three-phase generator 29. The latter can energize the radial field stator 28 with a rotary-field current which, by means of control of the load angle both with respect to its magnitude and its direction enables adjustment of the torque applied to the rotor 3 and stabilizes the latter.

The aforedescribed measuring unit 1 can be utilized in various ways. Thus it can be used for the measurement of the flow quantity of liquids and gases in conduits. In this case, the vanes 5, 6 are so configured that the liquid flowing through the annular channel between rotor 3 and support tube 2 rotates the rotor 3 at a speed proportional to the velocity of the liquid, whereby the flow speed is a measure of the volume of the throughflowing medium. Gaseous media flow can also be measured. The measurement of the speed of the rotor 3 can be effected for example by an inductive pulse tapping from the rotary field stator 28 where the spoked pole magnet 9 forms the pulse generator. For measurement precision it is advantageous that the rotor 3 is journaled frictionlessly and is practically not subject to any wear and thus requires no maintenance.

To the extent that the rotor 3 is formed without vanes 5, 6 and thus has a smooth cylindrical surface, the measuring apparatus 1 of the invention can also be used to measure the viscosity of gaseous or liquid media. For this purpose, the rotor 3 is driven with the aid of the rotary field generator 29 and the synchronous motor formed by the rotary field stator 28 and spoked pole magnet 9 and the electric power consumption of the synchronous motor for maintaining a certain rotor speed is measured. This is substantially proportional to the friction work at the surface of the rotor 3. The friction work in turn is again a measure of the viscosity of the medium surrounding the rotor 3.

Figure 2:
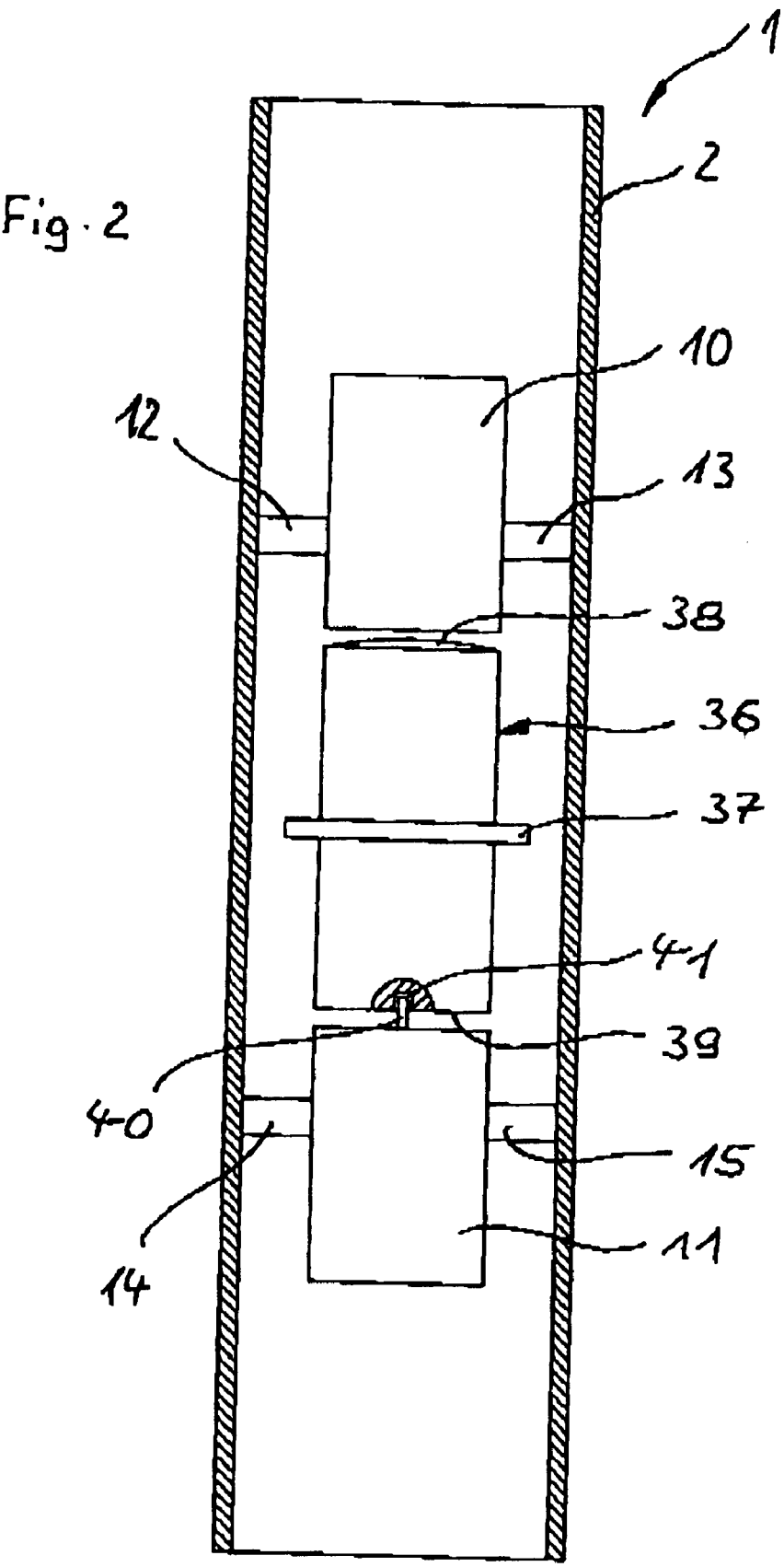
FIG. 2 is a longitudinal section through the combination of the support tube of the rotor in a second embodiment.

The embodiment according to FIG. 2 differs from that according to FIG. 1 only by another shape of the rotor, whereby parts lying externally of the support tube 2 are identical with those of the embodiment of FIG. 1 and have been omitted for clarity.

In FIG. 2, a rotor 36 is provided whose external contour differs from that of the rotor 3 according to FIG. 1 only in that it has a substantially smooth cylindrical outer surface at the axial center provided with the outwardly-projecting annular rib 37. This annular rib 37 forms a resistance in the flow of a medium through the support tube 2. As a result, an axial force is transmitted to the rotor 36 which gives rise to a shift in the axial position of the rotor 36. This is detected via the magnet coils 22, 23 and triggers an electric signal proportional to the axial shift in the control unit 27 that is also proportional to the flow velocity.

Since the axial force applied by the medium flowing through the rotor 36 is not only a function of the flow velocity of the medium but also of its viscosity, it is advantageous to also determine simultaneously the viscosity of the through-flowing medium. This occurs, as has already been described in connection with the smooth rotor 3, by imparting to the rotor 36 a rotary movement with the aid of the synchronous motor and detecting the drive power required for that purpose and utilizing the drive power as a measure of the viscosity of the throughflowing medium.

To avoid mechanical contact of the axially spaced portions of the rotor 36, the latter has a spherically configured end surface 38. As soon as contact occurs between rotor 36 and radial stabilizer 10, it is limited by this configuration to the central region at which there is a reduced peripheral speed. It will be self-understood that the lower end face can be correspondingly spherically shaped.

The lower radial stabilizer has, alternatively, in its axial center on its end face adjacent the rotor 36 a bearing pin 40 which engages in a bearing recess 41 in the rotor 36. Between bearing pin 40 and bearing recess 41 a play can be provided which, under normal radial deviations of the rotor 36, is sufficiently large that no contact occurs. Only when the radial deflection becomes excessive does the bearing pin 40 and bearing recess 41 limit further radial movement. Such a radial bearing can, as is self-understood, also be provided in the region of the upper radial stabilizer 10.

Figure 3:
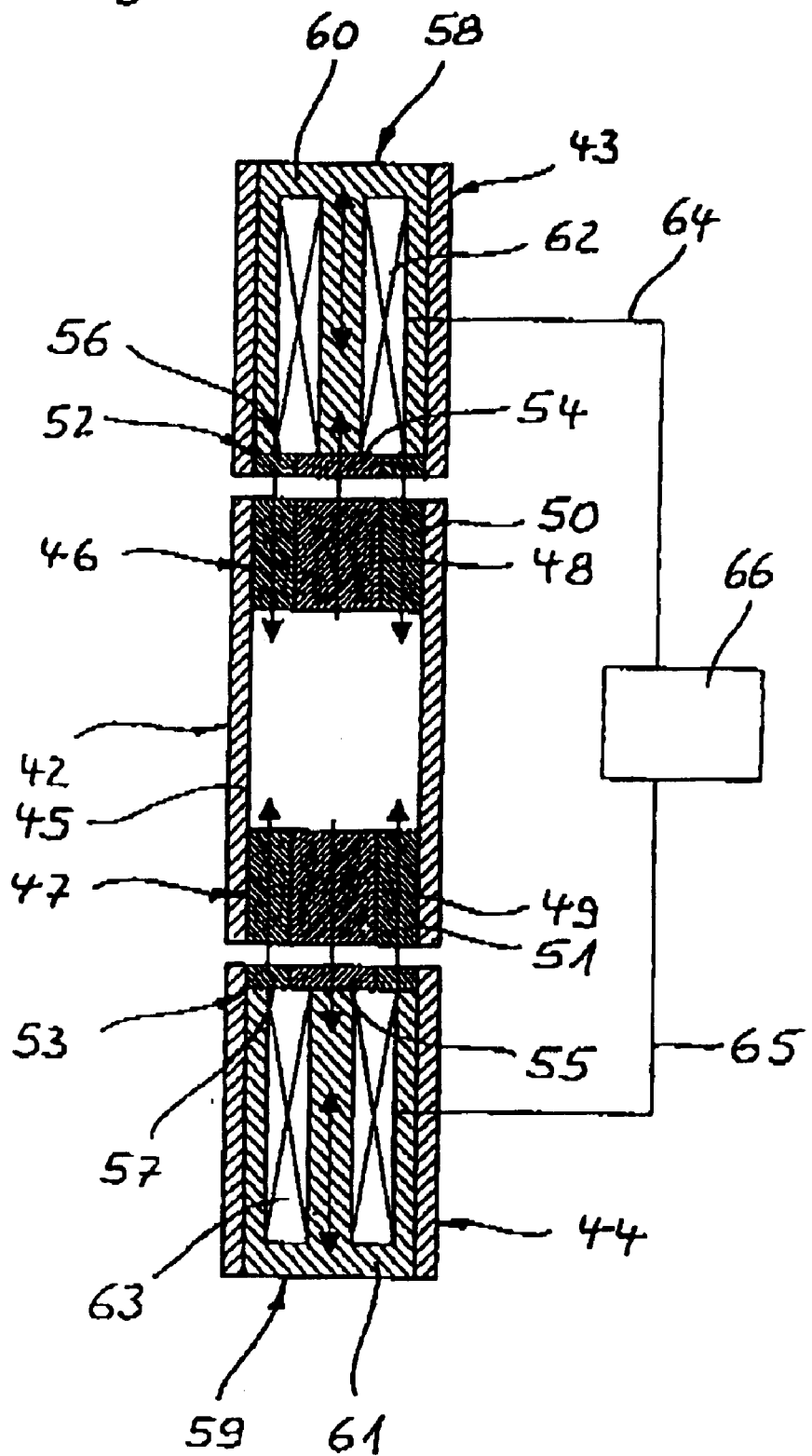
FIG. 3 is a longitudinal section through the combination of rotor hub and radial stabilizer in a third embodiment.

In the embodiment of FIG. 3, the support tube 2 with all of its associated parts, has been omitted for clarity. FIG. 3 shows a rotor 42 which is magnetically held between two radial stabilizers 43, 44. The rotor 42 has a smooth exterior with a rotor hub of circular cross section which cross section is extended by the radial stabilizers 43, 44. Not shown are the ribs 12, 13, 14, 15 which are shown in FIG. 1 and with which the radial stabilizers 43, 44 are affixed to the interior of the support tube 2.

The rotor 42 has at its ends respective rotor magnets 46, 47. Both rotor magnets 46, 47 are constructed to be bipartite. They comprise, respectively, cylinder-shaped inner magnets 48, 49 and a respective annular outer magnet 50, 51 respectively surrounding same. The outer magnets 50, 51 lie with their inner sides against the neighboring inner magnets 48 or 49.

The rotor magnets 46, 47 are each juxtaposed with a stator magnet 52, 53. The stator magnets 52, 53 are also constructed to be bipartite like the rotor magnets 46, 47, i.e. they each have a cylinder-shaped inner magnet 54, 55 and an annular outer magnet 56, 57 respectively surrounding same. The diameter of the inner magnets 54, 55 of the stator magnets 52, 53 correspond to the diameter of the inner magnets 48, 49 of the rotor magnets 46, 47 while the diameters of the outer magnets 56, 57 of the stator magnets 52, 53 are identical to the diameters of the outer magnets 50, 51 of the rotor magnets 46, 47. They are all coaxially arranged.

The rotor magnets 46, 47 and the stator magnets 52, 53 are so magnetized that the respective neighboring pairs of magnets are juxtaposed over their entire areas are attracting. The present embodiment is special in that the respective paired juxtaposed inner magnets 48, 54 or 49, 55 are magnetized away from the rotor 52 while the respective paired juxtaposed outer magnets 50, 56 or 51, 57 are magnetized axially in the direction toward the rotor 52, i.e. oppositely. This is symbolized by the arrows. The opposite magnetizations increases the stiffness of the journaling of the rotor 42 in the radial direction very substantially.

Cup-shaped coils 58, 59 are arranged in the radial stabilizers 43, 44 and are comprised respectively of a cup-shaped ferromagnetic yoke 60, 61 and an electric coil 62, 63 disposed therein. The yokes 60, 61 are open toward the stator magnets 52,53. The mean diameters of the coils 62, 63 correspond to the outer diameters of the respective neighboring inner magnets 54, 55. The coils 62, 63 are connected with a control device 66 via electrical conductors 64, 65. The control device 66 feeds the coils 62, 63 with excitation current. Depending upon the direction of the current, the axial magnetic flux in the gap between rotor 42 and radial stabilizers 43, 44 can be increased or weakened as is signified by the central double-headed arrows. In this manner the effective axial force is varied such that the rotor 42 is always positioned in the axial centered between the radial stabilizers 43, 44.

We claim:

1. An apparatus for measuring a property of a flowing fluid, comprising:

a support tube connectable in a path of a flowing fluid so as to be axially transversed by said fluid;

an elongated rotor rotatable in said support tube and spaced inwardly of a wall thereof whereby said flowing fluid passes between said rotor and said wall, said rotor having an exterior configured to be affected by said property of said fluid as said fluid flows past said surface upon transversing said support tube;

repsective axially magentic rotor members at opposite ends of said rotor;

respective axially magnetic stator members each paired with one of the rotor members to form a magnetic assembly therewith, axially juxtaposed with the respective rotor member and oppositely magnetically poled with respect to the respective rotor member to generate an attractive axial force between the stator member and the rotor member of each assembly;

respective supports mounting each of said stator members on said support tube, whereby said attractive axial forces between the stator member and the rotor member of each pair solely position said rotor axially and radially in said tube, at least one of the members of each pair being a permanently magnetic magnet and the other member of each pair being selected from a permanently magnetic magnet poled opposite the respective said one of said members and a magnetic flux guide piece; and an electromagnetic axially stabilizing device responsive to axial displacement of said rotor for generating a compensatory displacement thereof.

2. The apparatus defined in claim 1 wherein said other member of each pair is a magnetic flux guide piece.

3. The apparatus defined in claim 1 wherein both the rotor member and the stator member of each pair are permanent magnets.

4. The apparatus defined in claim 3 wherein each of said permanent magnets comprises an outer permanent magnet and an inner permanent magnet nested in said outer permanent magnet and magnetically poled in a direction opposite to that of said outer permanent magnet.

5. The apparatus defined in claim 2, further comprising electromagnet coils on said support tube positioned to increase magnetization of said magnetic flux guide pieces and thereby increase said forces.

6. The apparatus defined in claim 1 wherein said rotor has a hub, said rotor members being received within said hub at axially opposite ends thereof.

7. The apparatus defined in claim 6 wherein said stator members are received in radial stabilizers mounted on said support tube and having contours which do not project outwardly beyond said hub.

8. The apparatus defined in claim 7 wherein at least one end of said hub and the respective radial stabilizer are of spherical configuration.

9. The apparatus defined in claim 7 wherein at least one end of said hub and the respective radial stabilizer have respectively an axially extending pin and hole receiving said pin with radial clearance.

10. The apparatus defined in claim 1 wherein said electromagnet axially stabilizing device comprises at least one electromagnet coil, a sensor for detecting axial movement of said rotor and a control device connected to said sensor and said coil for influencing electric current flow in said coil so that a magnetic field of said coil counteracts movement of said rotor from a setpoint position.

11. The apparatus defined in claim 10 wherein said magnetic axially stabilizing device comprises two electromagnet coils, a respective one of said electromagnet coils being disposed on said support tube in a region of each of said stator members.

12. The apparatus defined in claim 1 wherein said rotor has a pulse generator and said support tube has a pulse pickup, the pulse generator producing pulses corresponding to a speed of said rotor.

13. The apparatus defined in claim 12 wherein said pulse generator has magnets and said pulse pickup is a coil.

14. The apparatus defined in claim 1 wherein said rotor has a radially magnetized spoke wheel magnet and said support tube is provided with a rotary field stator capable of being electrically energized to rotate said rotor.

15. The apparatus defined in claim 14 wherein said spoke wheel magnet has at least four magnetic segments magnetized in different radial directions.

16. The apparatus defined in claim 14, further comprising an electronic three-phase generator with load angle regulation connected to said stator for energizing same.

17. The apparatus defined in claim 1 wherein said exterior has a smooth symmetrical outer surface.

18. The apparatus defined in claim 17 wherein said exterior is formed with an annular rib and said apparatus includes a sensor responsive to an axial position of said rib for measurement of said property.

* * * * *